United States Patent
Sabouroux

(10) Patent No.: US 10,545,109 B2
(45) Date of Patent: Jan. 28, 2020

(54) PORTABLE DEVICE FOR MEASURING DIELECTRIC AND/OR MAGNETIC CHARACTERISTICS OF SAMPLES

(71) Applicants: CENTRE NATIONAL DE LA RECHERCHE SCIENTIFIQUE (CNRS), Paris (FR); UNIVERSITE D'AIX MARSEILLE, Marseilles (FR); ECOLE CENTRALE DE MARSEILLE, Marseilles (FR)

(72) Inventor: Pierre Sabouroux, Plan de Cuques (FR)

(73) Assignees: CENTRE NATIONAL DE LA RECHERCHE SCIENTIFIQUE (CNRS), Paris (FR); UNIVERSITE D'AIX MARSEILLE, Marseilles (FR); ECOLE CENTRALE DE MARSEILLE, Marseilles (FR)

( * ) Notice: Subject to any disclaimer, the term of this patent is extended or adjusted under 35 U.S.C. 154(b) by 124 days.

(21) Appl. No.: 15/576,414

(22) PCT Filed: May 25, 2016

(86) PCT No.: PCT/EP2016/061846
§ 371 (c)(1),
(2) Date: Nov. 22, 2017

(87) PCT Pub. No.: WO2016/189058
PCT Pub. Date: Dec. 1, 2016

(65) Prior Publication Data
US 2018/0156748 A1  Jun. 7, 2018

(30) Foreign Application Priority Data
May 25, 2015 (FR) ..................................... 15 54667

(51) Int. Cl.
*G01N 27/00* (2006.01)
*G01N 27/22* (2006.01)
*G01N 27/72* (2006.01)

(52) U.S. Cl.
CPC ........... *G01N 27/221* (2013.01); *G01N 27/72* (2013.01)

(58) Field of Classification Search
USPC ........................ 324/228, 331, 377, 627, 71.1
See application file for complete search history.

(56) References Cited

U.S. PATENT DOCUMENTS

| 3,753,092 A | 8/1973 | Ludlow et al. |
| 2004/0104736 A1 | 6/2004 | Cohen et al. |
| (Continued) | | |

FOREIGN PATENT DOCUMENTS

FR  2 976 086 A1  12/2012

OTHER PUBLICATIONS

International Search Report as issued in International Patent Application No. PCT/EP2016/061846, dated Jul. 12, 2016.

*Primary Examiner* — Vincent Q Nguyen
(74) *Attorney, Agent, or Firm* — Pillsbury Winthrop Shaw Pittman LLP

(57) ABSTRACT

A portable device includes first and second connectors capable of guiding an electromagnetic wave, a sample carrier installed between the first premier and second connectors and including a cavity housing a sample, an electronic module including an electromagnetic wave generator, and a processing system capable of analysing the electromagnetic wave exiting the second connector in order to deliver a first dielectric permittivity measurement and/or a second magnetic permeability measurement, a computer device including a control system capable of controlling the operation of the electronic module and of recovering each (Continued)

first or second measurement, and a portable container housing the first and second connectors, the sample carrier, the electronic module and the computer device.

13 Claims, 1 Drawing Sheet

(56) References Cited

U.S. PATENT DOCUMENTS

| | | | | |
|---|---|---|---|---|
| 2012/0218195 A1* | 8/2012 | Koh | ............... | G06F 1/169 |
| | | | | 345/173 |
| 2014/0014508 A1* | 1/2014 | Terashima | ............ | G01N 27/327 |
| | | | | 204/403.01 |
| 2015/0061670 A1* | 3/2015 | Fordham | .............. | G01N 24/081 |
| | | | | 324/309 |

\* cited by examiner

PORTABLE DEVICE FOR MEASURING DIELECTRIC AND/OR MAGNETIC CHARACTERISTICS OF SAMPLES

CROSS-REFERENCE TO RELATED APPLICATIONS

This is the U.S. National Stage of PCT/EP2016/061846, filed May 25, 2016, which in turn claims priority to French Patent Application No. 1554667, filed May 25, 2015, the entire contents of all applications are incorporated herein by reference in their entireties.

FIELD

The invention relates to measurements of dielectric and/or magnetic characteristics of samples.

BACKGROUND

As those skilled in the art know, electromagnetic waves are increasingly present in the environment, and the consequences of their interactions with living beings and materials present in this environment are often very poorly known and often difficult to access. There thus exists an important need to understand these interactions, and notably for quantification in order to better manage them.

To achieve this understanding, at least partially, it is possible to use analysis electromagnetic waves and to deduce, from variations in these electromagnetic waves induced from their interactions with the material analysed, values of dielectric or magnetic characteristics of said material such as for example the dielectric permittivity ($\varepsilon$) or the magnetic permeability ($\mu$).

In order that this type of electromagnetic analysis is reliable, it is indispensable that the material analysed is not perturbed by parasites and notably by parasitic electromagnetic waves, different to those used to analyse it. In other words, the material analysed has to be located in a controlled environment, which, until now, has imposed the use of electromagnetic wave transport equipment and measurement equipment (sometimes called network analysers) which are quite bulky and thus generally fixedly installed in a room (generally a laboratory) and, what is more, not dedicated to a single type of analysis.

When the analysis instrumentation cannot be moved, it is difficult to transport it without risk of damage, and thus it is necessary to bring the material to analyse to the place where said instrumentation is installed, which is frequently impossible (in particular when the material is not transportable) or restrictive. In addition, due to the fact that it is not dedicated to a single type of analysis, it is often used and thus often unavailable.

When the analysis instrumentation can be moved, it is then greatly used due to its numerous applications and thus not available all the time.

Moreover, since current analysis instrumentation are often complex to use and the results of their analyses are often complex to interpret or to understand, they can only be used by specialists.

In addition, current analysis instrumentation are often costly and thus relatively rare.

The document US 2004/104736 A1 (Cohen et al.) discloses a device making it possible to measure the dielectric characteristics of liquid samples. The device comprises two connectors capable of guiding an electromagnetic wave, an electric module comprising a generator capable of generating the wave and processing means capable of analysing it. The spectral domains mentioned extend up to 500 MHz, or even up to several GHz. However, a capacitive system, by design, operates at a determined resonance frequency. In other words, capacitive techniques are monochromatic. The device described here is a Q-meter which thus can only, at best, operate at determined discrete frequencies and not over a continuous frequency range. It may thus make it possible to measure the dielectric permittivity, but not the magnetic permeability.

The document U.S. Pat. No. 3,753,092 (Ludlow et al.) also only addresses liquid samples. The capacitive technique used does not work at high frequencies since it implements a L-C circuit which, by its very principle, is a low frequency device, operating on the basis of determined time constants. The wave generator is a QCSW (Quartz Crystal Square Wave) generator, which operates at fixed and low value frequency, thus uniquely suitable for the analysis of liquid samples.

SUMMARY

The aim of the invention is to improve the situation.

It proposes to this end a portable device, intended to measure dielectric and/or magnetic characteristics of samples, and comprising for this purpose:
  first and second connectors capable of guiding an electromagnetic wave along a reference axis,
  a sample carrier installed in a detachable manner between the first and second connectors and comprising a cavity capable of housing a sample in a position enabling the electromagnetic wave to pass through it,
  an electronic module comprising a generator capable of generating the electromagnetic wave, and processing means capable of analysing the electromagnetic wave exiting the second connector in order to deliver a first measurement representative of a dielectric permittivity of the sample and/or a second measurement representative of a magnetic permeability of the sample,
  a computer device comprising a screen, a human/machine interface and control means capable of controlling the operation of the electronic module and of recovering each first or second measurement at least to display it on the screen, and
  a portable container and housing the first and second connectors, the sample carrier, the electronic module and the computer device.

A device exclusively dedicated to measurements of dielectric permittivity and magnetic permeability is thereby made available, which can be easily transported to virtually any spot, and which is very easy to use, including by non-specialists of electromagnetic measurements.

The portable device according to the invention may comprise other characteristics which may be taken separately or in combination, and notably:
  its container may also house extractible data storage means coupled to the computer device and in which said device stores the analysis results;
  its container may also house a printer coupled to the computer device;
  its container may also house a battery capable of supplying with current the electronic module and the computer device, as well as the optional extractible data storage means and the optional printer;
  its container may comprise a space capable of receiving at least one accessory;

its computer device may be rotationally mounted in a part of the container;

the screen may be of touch-screen type and in this case comprises a part of the human/machine interface;

its sample carrier may comprise, around the cavity, measurement means capable of measuring at least one intrinsic characteristic of the sample and/or action means capable of making this intrinsic characteristic vary;

its sample carrier may comprise a body in which the cavity is defined and comprising an inlet and outlet communicating with the cavity and enabling a circulation of a fluid constituting at least partially the sample;

its sample carrier may comprise two side walls, optionally detachable, and laterally closing the cavity substantially transversally to the reference axis;

the side walls may be made of at least one dielectric material transparent to the propagation of the electromagnetic wave;

the frequency of the electromagnetic wave generated by the generator may be comprised within an interval of frequencies ranging from several kilohertz (kHz) to several gigahertz (GHz) or several tens of gigahertz;

for example, the frequency of the electromagnetic wave generated by the generator is comprised within an interval of frequencies equal to [1 GHz-18 GHz]; and, the generator may be controlled in such a way that the frequency of the electromagnetic wave generated scans the interval of frequencies in a continuous manner (for example if the generator is an analogue generator) or quasi-continuous manner (for example if the generator is a digital generator).

BRIEF DESCRIPTION OF THE DRAWINGS

Other characteristics and advantages of the invention will become clear from examining the description detailed hereafter, and the appended drawings, in which.

DETAILED DESCRIPTION

The aim of the invention is notably to propose a portable measuring device 1 intended to provide measurements of dielectric and/or magnetic characteristics of samples 2.

Figure 1:
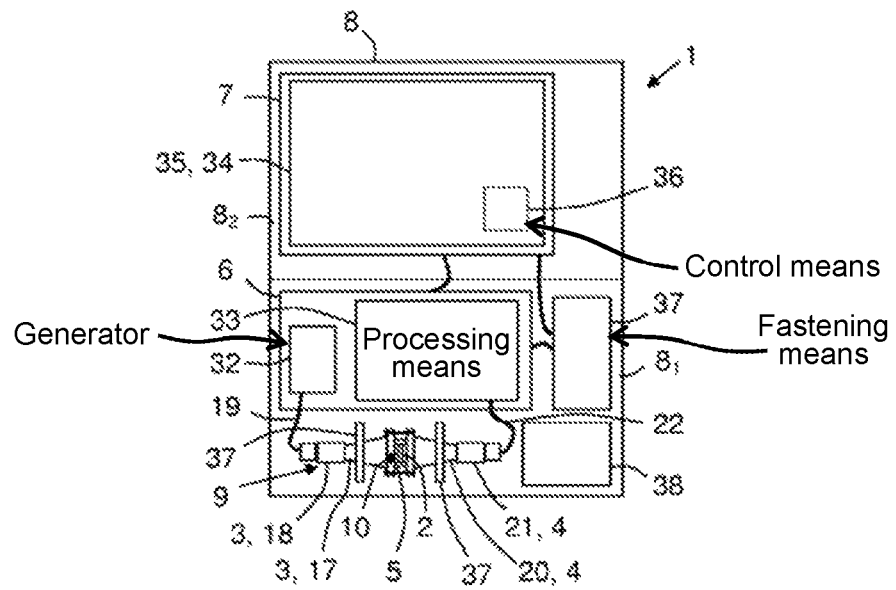
FIG. 1 illustrates in a schematic and functional manner an exemplary embodiment of a portable measuring device according to the invention.

In FIG. 1 is schematically and functionally illustrated a non-limiting exemplary embodiment of a portable measuring device 1, according to the invention. As illustrated, such a device (for portable measurement) 1 comprises at least first 3 and second 4 connectors, a sample carrier 5, an electronic module 6, a computer device 7, and a portable container 8.

The portable container 8 houses, preferably in predefined places, at least the first 3 and second 4 connectors, the sample carrier 5, the electronic module 6 and the computer device 7. As illustrated in a non-limiting manner in FIG. 1, this container 8 may be arranged in the form of a suitcase or a briefcase. In this case, it comprises at least first $8_1$ and second $8_2$ parts, for example rotationally mounted with respect to each other.

In the example illustrated in a non-limiting manner in FIG. 1, the first part $8_1$ notably comprises the first 3 and second 4 connectors, the sample carrier 5, and the electronic module 6, and the second part $8_2$ comprises the computer device 7. But any other distribution of the different elements 3-7 of the device 1 may be envisaged in the first $8_1$ and second $8_2$ parts, notably so as to improve the compactness of the portable container 8.

Furthermore, the respective positions of the elements 3-7 within the first $8_1$ and second $8_2$ parts are not limited to those that are illustrated in FIG. 1, only as an example. For example, the electronic module 6 may be placed in a lower part of the first part $8_1$, and the first 3 and second 4 connectors and the sample carrier 5 may be placed in an upper part of the first part $8_1$, placed above this lower part.

It will be noted that in order to protect efficiently the elements 3-7, notably during movements of the device 1, it is particularly advantageous that the first $8_1$ and second $8_2$ parts of the portable container 8 comprise foam parts comprising housings of shapes adapted respectively to the shapes and/or functionalities of the elements 3-7.

For example, this portable container 8 may have a length less than around 60 cm, a width less than around 50 cm, and a height (once closed) less than around 30 cm. The objective here is to optimise the compactness.

Figure 2:
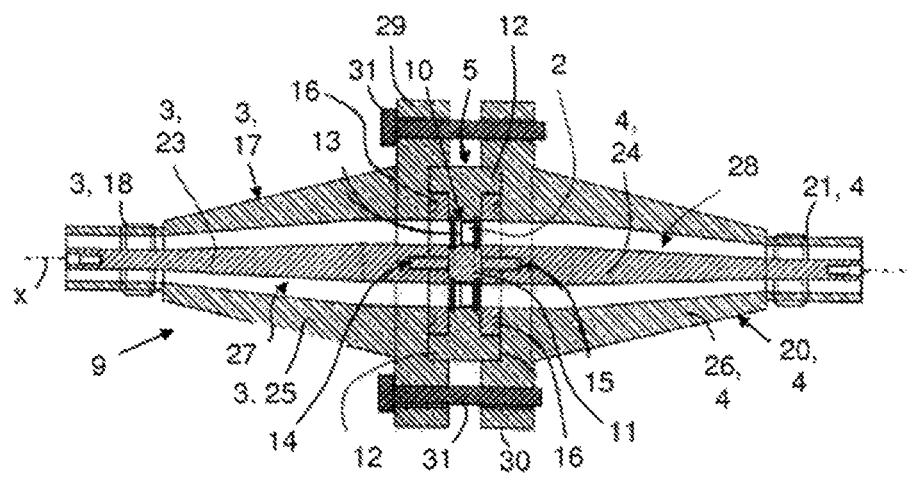
FIG. 2 illustrates in a schematic manner, in sectional view, an exemplary embodiment of an assembly, constituted of a sample carrier and connectors, and being able to form part of a portable measuring device according to the invention.

The first 3 and second 4 connectors and the sample carrier 5 constitute, once assembled, an assembly 9 which is better illustrated in FIG. 2. It will be noted that the non-limiting example of assembly 9 which is illustrated in FIG. 2 is described in detail in the patent document FR 2976086. Consequently, this assembly 9 will not be described in detail hereafter, but all the technical details and options described in this patent document FR 2976086 may apply to the assembly 9 described below.

The first 3 and second 4 connectors are each capable of guiding an (analysis) electromagnetic wave along a reference axis x.

The sample carrier 5 is installed in a detachable manner between the first 3 and second 4 connectors and comprises a cavity 10 which is capable of housing a sample 2 in a position that enables each (analysis) electromagnetic wave from the first connector 3 to pass through it.

It will be noted that in FIG. 2 the reference axis x constitutes an axis of revolution of the parts represented.

As illustrated, the sample carrier 5 comprises more precisely a central core 11 made of electrically conducting material and a tubular outer body 12, surrounding the central core 11, coaxially to the reference axis x and made of electrically conducting material. It (5) also comprises assembly means 16 made of electrically conducting and leak tight material capable of joining to the central core 11 and/or to the outer body 12, in a manner leak tight to gases and/or to liquids, side walls 13 which laterally close the cavity 10 (which is also delimited by the central core 11 and the outer body 12).

The central core 11 here has, along the reference axis x, first and second ends situated on either side of its central part and capable of being housed in housings 14 and 15 defined respectively in the first 3 and second 4 connectors.

The side walls 13 are made of at least one dielectric material and transparent to the analysis electromagnetic waves, such as for example Teflon or polyvinyl chloride (or PVC). They are for example in disc shape and mounted on a central part of the central core 11.

In the configuration illustrated in a non-limiting manner, the side walls 13 are detachable with respect to the outer body 12 and to the central core 11, due to the fact that the sample 2 is not a fluid material. But in an alternative embodiment, not illustrated, the sample 2 could be a fluid (or runny) material. In this case, the outer body 12 must comprise an inlet and outlet communicating with the cavity 10 and enabling circulation of a fluid constituting at least partially the sample 2. It will be noted that the fluid may be introduced to be analysed statically or instead it may circulate to be analysed dynamically. It is thereby possible to carry out continuous measurements over time, for example to determine variations in characteristic(s) in real time.

The sample carrier 5 thus makes it possible to analyse the dielectric and/or magnetic characteristics of materials of samples 2 of very diverse types, and notably materials that are solid, granular, powdery, liquid or in gel form.

The first connector 3 here comprises first guiding means 17 intended to guide the analysis electromagnetic wave along the reference axis x, and a first connection means 18 fixedly joined to a first end of the first guiding means 17 and connected to one of the connection means of a first coaxial cord 19 intended to supply it with electromagnetic waves.

The second connector 4 here comprises second guiding means 20 intended to guide the analysis electromagnetic wave along the reference axis x, and a second connection means 21 fixedly joined to a first end of the second guiding means 20 and connected to one of the means of connection of a second coaxial cord 22 intended to transfer each electromagnetic wave having passed through the sample 2 to the electronic module 6.

These first 17 and second 20 guiding means each comprise a central core 23 or 24 made of an electrically conducting material, and a tubular body 25 or 26 made of an electrically conducting material and surrounding the associated central core 23 or 24. Each electromagnetic wave may thus circulate in the space 27 or 28 which is defined between a central core 23 or 24 and an associated tubular body 25 or 26.

The housings 14 and 15 are defined respectively in the two central cores 23 and 24.

Furthermore, each tubular body 25 or 26 comprises a first end 29 or 30, which is opposite to a second end joined to a first 18 or second 21 connection means, and which comprises a shoulder capable of housing tightly and partially the outer body 12 of the sample carrier 5.

The joining between the first 3 and second 4 connectors, which is intended to immobilise precisely the sample carrier 5, is ensured by fastening means which may, for example, be screws. As a non-limiting example, it is possible, as illustrated, to use at least two screws 31 which pass through holes defined in the first ends 29 and 30 of the tubular bodies 25 and 26.

Although it does not appear in FIG. 2, the sample carrier 5 may also and optionally comprise around the cavity 10 measurement means capable of measuring at least one intrinsic characteristic of the sample 2 and/or action means capable of making this intrinsic characteristic vary.

For example, the measurement means may be arranged to measure the temperature of the sample 2. In this case, the measurement means may comprise a temperature probe housed in the outer body 12 of the sample carrier 5 and connected to an external thermometer.

Also for example, the action means may be arranged to make the temperature of the sample carrier 5, and thus the sample 2, vary. In this case, the action means may comprise a heating resistor housed in the outer body 12 of the sample carrier 5 and controlled electrically.

As illustrated in a non-limiting manner in FIG. 1, the first part $8_1$ of the container 8 may advantageously comprise fastening means 37 intended to immobilise the assembly 9, notably during transport of the device 1. These fastening means 37 may, for example, be straps (optionally elastic) or rotationally mounted or clipped legs or instead flanges (or collars).

The electronic module 6 comprises at least one generator 32 and processing means 33.

The generator 32 is capable of generating each electromagnetic wave over a wide frequency range, for example over a continuous domain ranging from several kilohertz (kHz) to several gigahertz (GHz) or several tens of GHz. These waves are intended to, and suited to, analysing the electromagnetic properties (magnetic permeability and dielectric permittivity) of a sample 2. This is obtained by supplying the first connector 3 via the first coaxial cord 19 (which is provided with its own connection means), with the waves generated by the generator 32.

In one embodiment, the frequency range of the waves thereby generated is equal to [1 GHz-18 GHz], which corresponds in particular to the frequency range enabling the measurement of the magnetic permeability of samples in the envisaged applications, according to the transmission/reflection measurement technique.

In one embodiment, the generator may be controlled in such a way that the frequency of the electromagnetic wave generated scans the interval of frequencies considered. This scanning may be carried out in a continuous or quasi-continuous manner. The expression "quasi-continuous", compared to the expression "continuous", refers to embodiments in which the generator may be a digital generator, such as an analogue frequency digital synthesizer. Indeed, strictly speaking, a "continuous" scanning of the frequency range assumes an analogue generator.

The processing means 33 are capable of analysing each electromagnetic wave exiting the second connector 4 (after having passed through the sample 2), in order to deliver a first measurement which is representative of a dielectric permittivity (c) of this sample 2 and/or a second measurement which is representative of a magnetic permeability (p) of this sample 2. For example, these processing means 33 are capable of carrying out so-called "vector" type analyses, well known to those skilled in the art. In this case, the processing means 33 determine the coefficient of reflection (R) and the coefficient of transmission (T), and conventionally deduce from these coefficients R and T the complex dielectric permittivity (c) and/or the complex magnetic permeability (p). It will be noted that they can next, optionally, deduce from the complex dielectric permittivity (c) and the complex magnetic permeability (p) the complex conductivity of the sample 2 and/or the loss tangent (commonly called delta) which corresponds to the ratio between the real and imaginary parts of the complex permittivity.

But other types of analysis may be used from the moment that they make it possible to obtain measurements representative of the dielectric permittivity (c) and measurements representative of the magnetic permeability (p).

As a non-limiting example, the electronic module 6 may be that which is sold by the Anritsu company.

The computer device 7 comprises at least one screen 34, a human/machine interface 35 and control means 36. Said means (36) are capable of controlling the operation of the electronic module 6 and of recovering each first or second measurement (carried out by the processing means 33) at least to display it on the screen 34.

For example, this computer device 7 may be a laptop computer or a tablet computer. It will be noted that this computer device 7 may potentially be rotationally mounted in a part of the container 8 (here the second 8$_2$) so as to facilitate the observation of the screen 34 when this container 8 is open and when a sample analysis must be carried out or is underway.

The control means 36 are arranged to allow a user of the device 1 to control the electronic module 6, in order, notably, to carry out calibrations at the start of a series of analyses, to define each analysis, to access the measurements via the screen 34 and optionally to exploit the measurements.

These control means 36 are preferably provided in the form of software modules (or computer modules or "software"). But they could also be provided in the form of a combination of electronic circuits (or "hardware") and software modules.

Also for example, the screen 34 may advantageously be of touch screen type. In this case, it comprises a touch screen comprising a part of the human/machine interface 35.

It will be noted that the human/machine interface 35 is intended to allow a user of the device 1 to control the operation of the computer device 7, and the electronic module 6 (via the control means 36 of the computer device 7). Consequently, it may comprise a control keyboard with keys and/or which is touch-sensitive, as well as optionally a mouse (or any equivalent means).

Although this does not appear in FIG. 1, the container 8 may optionally and also comprise extractible data storage means, such as for example a small hard disc, coupled to the computer device 7 and in which said device (7) can store the results of each analysis. Such a data storage means may next be extracted from the container 8, then transported with a view to being coupled to another computer device 7 intended to analyse and/or to use the analysis results that it stores.

Furthermore, and although this does not appear in FIG. 1, the container 8 may also and optionally house a printer coupled to the computer device 7. This may in fact make it possible to print out some at least of the results of the analyses carried out by the electronic module 6 and/or by the control means 36 from the measurements carried out by the electronic module 6, at the location where the analyses are carried out. But when a maximum of compactness is sought, such a printer may be omitted.

For example, this optional printer may be housed in the first part 8$_1$ of the container 8, between the electronic module 6 and the assembly 9, or instead under the electronic module 6.

It will be noted that the operation of the electronic module 6 and the computer device 7, as well as the optional extractible data storage means and the optional printer, require that they are supplied with current. To this end, the device 1 may, for example, comprise an internal electric transformer to which are connected the electronic module 6 and the computer device 7, as well as the optional extractible data storage means and the optional printer, and an electric power supply cable preferably detachable and connected to this electric transformer.

Furthermore, and as illustrated in a non-limiting manner in FIG. 2, the container 8 may also and optionally house a battery 37 capable of supplying with current the electronic module 6 and the computer device 7, as well as the optional printer. This option advantageously makes it possible to use the device 1 in places where there is no electricity or when the electrical socket locally available is incompatible with the connection means of the electric power supply cable of the device 1. In the example illustrated in a non-limiting manner in FIG. 1, the battery 37 is housed in the first part 8$_1$. But it could be housed in the second part 8$_2$.

It will also be noted that the container 8 may optionally comprise at least one space 38 capable of receiving at least one accessory. In the example illustrated in a non-limiting manner in FIG. 1, the space 38 is defined in the first part 8$_1$. But it could be defined in the second part 8$_2$.

Among the accessories that may be housed in the space 38, a sample carrier 5 suited to the circulation of a fluid and the electric power supply cable may notably be cited.

In another embodiment, the sample carrier 5 and its support 9 may be used in a configuration that is detached from the remainder of the portable device, that is to say not housed in the container 8. Apart from the fact of improving the compactness of the part of the portable device not comprising the sample carrier, this type of embodiment has several advantages:

The detached sample carrier enables an in situ analysis, at the heart of the environment of the sample measured, while isolating the electromagnetic wave generation and analysis means of the portable device from electromagnetic perturbations of said environment, thanks to the container 8. In the case of an environment detrimental to the measurement (having conditions likely to damage the device or to influence the measurement through parasitic electromagnetic waves), the analysis device may be protected as a whole and more particularly the processing means (a vector analyser for example) using for example a shielded type container. The connection of the sample carrier to the portable device then takes place, in the case of such an embodiment, through connectors connected to the core of the container, for example, by shielded coaxial cords and leak tight openings provided for this purpose.

Another advantage resides in the fact that a detached use of the sample carrier makes it possible to use several sample carriers in parallel. This may be carried out by connecting the sample carriers to the portable device through several independent connectors and by providing a switch making it possible to select the sample carrier used for the analysis. This type of "multichannel" analysis makes it possible to extract a set of dielectric and/or magnetic characteristics from a same material in different configurations (for example temperature) or of different materials measured in parallel. The processing of the data gathered may for example take place by multiplexing.

Thus, it is possible to control and/or to adjust and/or to optimise in real time the dielectric and/or magnetic characteristics of the material(s) of the samples, and to do so throughout the measurement method at any instant and as a whole.

The invention is not limited to the embodiments of portable measuring device described above, only as an example, but it encompasses all the alternatives that those skilled in the art could envisage within the sole scope of the following claims.

The invention claimed is:

1. A portable device for measuring dielectric and/or magnetic characteristics of samples, the portable device comprising i) first and second connectors adapted to guide an electromagnetic wave along a reference axis (x), ii) a sample carrier installed in a detachable manner between said first and second connectors and comprising a cavity adapted to house a sample in a position enabling said electromagnetic wave to pass through it, iii) an electronic module connected to the first and second connectors and comprising a generator adapted to generate said electromagnetic wave, and a processing system adapted to analyse said electromagnetic wave exiting said second connector in order to deliver a first measurement representative of a dielectric permittivity of said sample and/or a second measurement representative of a magnetic permeability of said sample, iv) a computer device coupled to the electronic module and comprising a screen, a human/machine interface and a control system adapted to control operation of said electronic module and to recover each first or second measurement at least to display it on said screen, and v) a portable container housing said first and second connectors, said sample carrier, said electronic module and said computer device.

2. The device according to claim 1, wherein said container also houses an extractible data storage system coupled to said computer device and in which said device stores the analysis results.

3. The device according to claim 2, wherein said container also houses a battery capable of supplying with current said electronic module and said computer device, as well as said optional extractible data storage system.

4. The device according to claim 1, wherein said container comprises a space adapted to receive at least one accessory.

5. The device according to claim 1, wherein said computer device is movable in said container.

6. The device according to claim 1, wherein said screen is a touch screen and comprises a part of said human/machine interface.

7. The device according to claim 1, wherein said sample carrier comprises around said cavity a measurement system adapted to measure at least one intrinsic characteristic of said sample and/or an action system capable of making said intrinsic characteristic vary.

8. The device according to claim 1, wherein said sample carrier comprises a body in which is defined said cavity and comprising an inlet and outlet communicating with said cavity and enabling circulation of a fluid constituting at least partially said sample.

9. The device according to claim 1, wherein said sample carrier comprises two side walls laterally closing said cavity substantially transversally to said reference axis.

10. The device according to claim 9, wherein said side walls are made of at least one dielectric material transparent to the propagation of said electromagnetic wave.

11. The device according to claim 1, wherein a frequency of the electromagnetic wave generated by the generator is comprised within an interval of frequencies ranging from several kilohertz to several gigahertz or several tens of gigahertz.

12. The device according to claim 11, wherein the frequency of the electromagnetic wave generated by the generator is comprised within an interval of frequencies equal to [1 GHz-18 GHz].

13. The device according to claim 11, wherein the generator is controlled in such a way that the frequency of the electromagnetic wave generated scans the interval of frequencies in a continuous or quasi-continuous manner.

* * * * *